(12) United States Patent
Ehman et al.

(10) Patent No.: US 8,072,216 B2
(45) Date of Patent: Dec. 6, 2011

(54) SHEAR WAVE GENERATION SYSTEM FOR MEDICAL IMAGING

(75) Inventors: Richard L. Ehman, Rochester, MN (US); Meng Yin, Rochester, MN (US); Kevin J. Glaser, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 273 days.

(21) Appl. No.: 12/418,218

(22) Filed: Apr. 3, 2009

(65) Prior Publication Data
US 2009/0295387 A1 Dec. 3, 2009

Related U.S. Application Data

(60) Provisional application No. 61/042,437, filed on Apr. 4, 2008.

(51) Int. Cl.
*G01V 3/00* (2006.01)
(52) U.S. Cl. .......................................... 324/318
(58) Field of Classification Search .......... 324/300–322; 600/410–435
See application file for complete search history.

(56) References Cited

U.S. PATENT DOCUMENTS

| | | | | |
|---|---|---|---|---|
| 4,897,604 A * | 1/1990 | Carlson et al. | ................. | 324/318 |
| 5,351,688 A * | 10/1994 | Jones | ............................. | 600/422 |
| 5,952,828 A * | 9/1999 | Rossman et al. | ............... | 324/318 |
| 5,961,003 A * | 10/1999 | Coryell | .......................... | 222/175 |
| 6,011,393 A * | 1/2000 | Kaufman et al. | ............. | 324/318 |
| 6,144,203 A * | 11/2000 | Richard et al. | ................ | 324/318 |
| 6,169,400 B1 * | 1/2001 | Sakuma | ......................... | 324/318 |
| 6,693,428 B2 * | 2/2004 | Udo et al. | ...................... | 324/318 |
| 6,746,049 B2 * | 6/2004 | Pavlov et al. | ................. | 280/803 |
| 6,778,849 B1 * | 8/2004 | Ninomiya et al. | ............ | 600/422 |
| 7,034,534 B2 * | 4/2006 | Ehman et al. | ................. | 324/318 |
| 7,307,423 B2 * | 12/2007 | Ehman et al. | ................. | 324/318 |
| 7,728,591 B2 * | 6/2010 | Weizenecker et al. | ........ | 324/318 |
| 7,733,087 B2 * | 6/2010 | Schuster et al. | .............. | 324/318 |
| 2005/0270029 A1 * | 12/2005 | Ehman et al. | ................. | 324/318 |

OTHER PUBLICATIONS

Olivier Rouviere et al; MR Elastography of the Liver: Preliminary Results; Radiology: vol. 240: No. 2—Aug. 2006; pp. 440-448.
Meng Yin et al; Assessment of Hepatic Fibrosis with Magnetic Resonance Elastography; Clinical Gastroenterology and Hepatology 2007; vol. 5, No. 10; 5:1207-1213.
Bensamoun et al, Determination of Thigh Muscle Stiffness Using Magnetic Resonance Elastography, Journal of Magnetic Resonance Imaging 23:242-247 (2006).

* cited by examiner

*Primary Examiner* — Dixomara Vargas
(74) *Attorney, Agent, or Firm* — Quarles & Brady LLp (57) ABSTRACT

A system is configured to produce a stress on a subject while performing a magnetic resonance elastography scan in a magnetic resonance imaging (MRI) system. The system includes an active driver operable to produce an energy configured for a magnetic resonance elastography (MRE) process. A passive actuator is configured to be positioned in the MRI system and to be coupled to the subject. The system includes a tube coupling the active driver to the passive actuator to deliver the energy produced by the active driver to the passive actuator, and a strap coupled to the passive actuator. The strap is configured to be disposed around the subject. The strap includes a substantially inelastic material configured to convert the energy delivered to the passive actuator from the tube into shear waves with the subject for use in the MRE process.

19 Claims, 6 Drawing Sheets

SHEAR WAVE GENERATION SYSTEM FOR MEDICAL IMAGING

CROSS-REFERENCE TO RELATED APPLICATIONS

This application is based on, claims the benefit of, and incorporates by reference U.S. Provisional Application Ser. No. 61/042,437 filed Apr. 4, 2008, and entitled "SYSTEM AND METHOD FOR MAGNETIC RESONANCE ELASTOGRAPHY."

STATEMENT REGARDING FEDERALLY SPONSORED RESEARCH

This invention was made with government support under Grant No. EB001981 awarded by the National Institutes of Health. The United States Government has certain rights in this invention.

BACKGROUND OF THE INVENTION

The field of the invention is medical imaging methods and systems. More particularly, the invention relates to devices for implementing magnetic resonance elastography (MRE).

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging (MRI) systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs that the physician can feel, and many diseased internal organs go undiagnosed unless the disease happens to be detectable by one of the above imaging modalities. Tumors, for example, of the liver, that are undetected by existing imaging modalities and cannot be reached for palpation through the patient's skin and musculature, are often detected by surgeons by biopsy or direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography (MRE). The method requires that the oscillating stress produce shear waves that propagate through the organ, or tissues to be imaged. These shear waves alter the phase of the MR signals, and this information can be used to determine the mechanical properties of the subject. In many applications, the production of shear waves in the tissues is merely a matter of physically vibrating the surface of the subject with an electromechanical device such as that disclosed in U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

A number of driver or actuator devices have been developed to produce the oscillatory force needed to practice MRE. As disclosed in U.S. Pat. Nos. 5,977,770, 5,952,828, 6,037,774, and 6,486,669, these typically include a coil of wire through which an alternating current flows. This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

Yet another approach is to employ an acoustic driver system as described in U.S. Pat. Nos. 7,034,534 and 7,307,423. The acoustic driver system includes an active driver located remotely from the MRI system and acoustically coupled by a tube to one or more passive drivers positioned on the subject being imaged. The passive drivers do not disturb the magnetic fields and may be oriented in any direction.

In many cases, the vibrations generated by the passive drivers are not efficiently communicated to a subject's internal organs. Some internal organs are isolated from the wall of a subject's body which further reduces the transfer of energy between the driver and the target organ. The abdomen, for example, includes many structures that result in inefficient transfer of energy from a passive driver to the internal organs. Both the parietal and visceral peritoneum, for example, operate to isolate abdominal organs such as the kidneys and liver. Accordingly, a passive driver placed over the abdomen has limited capability to generate shear waves through the abdomen, resulting in the abdominal organs being isolated from external vibration.

SUMMARY OF THE INVENTION

The present invention is a system for producing a stress on a subject while performing a magnetic resonance elastography scan in a magnetic resonance imaging (MRI) system. The system includes an acoustic driver capable of producing acoustic energy configured for a magnetic resonance elastography (MRE) procedure, a passive actuator configured to be positioned in the MRI system and coupled to the subject, and a tube coupling the driver to the actuator to deliver the energy produced by the driver to the actuator. The system includes a strap coupled to the actuator and configured to be disposed around the subject. The strap includes a substantially inelastic material configured to convert the energy delivered to the actuator from the tube into shear waves within the subject for use in the MRE process.

In an alternative embodiment, the present invention is a system for producing a stress on a subject undergoing an imaging procedure. The system includes an actuator configured to be disposed over the thorax of the subject. The actuator is configured to receive energy to be applied to the subject of an examination. The system includes a strap configured to be disposed around the subject. The strap includes a substantially inelastic material and is coupled to the actuator. The acoustic energy produces cyclic variations of a tension of the strap and the energy received by the actuator is delivered into the subject to generate shear waves within the subject positioned for magnetic resonance elastography (MRE) imaging.

In an alternative embodiment, the present invention is a method of generating shear waves within the abdomen of a subject for medical imaging using an actuator for magnetic resonance elastography (MRE). The method includes positioning the actuator against the body wall of the thorax of the subject over the ribcage of the subject. The actuator is configured to receive acoustic energy. The method includes securing a strap around the circumference of the subject and over the actuator to hold the actuator against the body wall of the subject. The strap includes a substantially inelastic material. The method includes transmitting acoustic energy to the actuator to generate mechanical vibrations of the actuator, and using the mechanical vibrations of the actuator to generate cyclic variations of the tension of the strap. The cyclic variations of the tension of the strap are communicated to the ribcage of the subject. The ribcage thusly generates pressure variations within the abdomen of the subject which are communicated to internal organs of the abdomen of the subject for MRE of an internal organ of the abdomen of the subject.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

The present invention is described in one or more embodiments in the following description with reference to the Figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Figure 1:
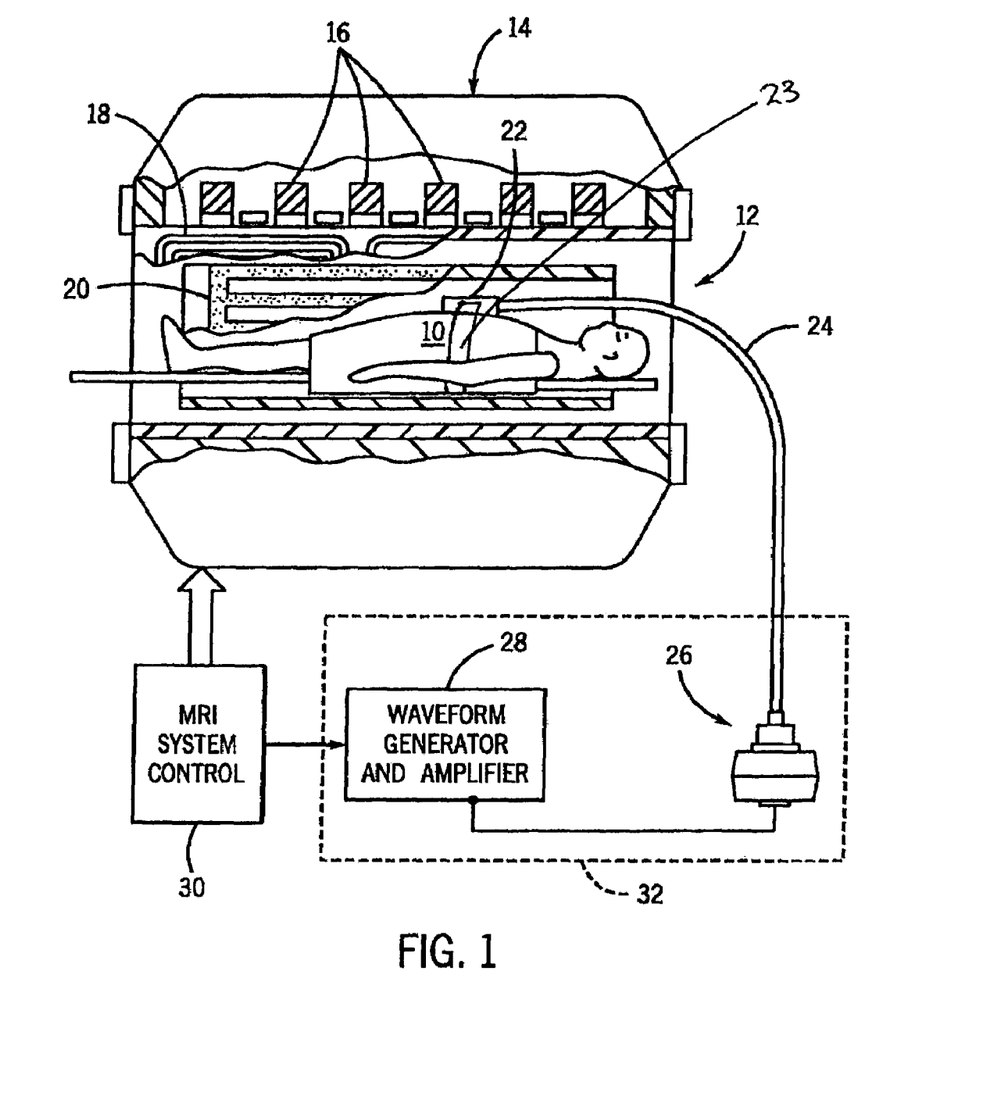
FIG. 1 is a pictorial representation of an MRI system including a strap positioned around the circumference of the subject over a passive actuator in accordance with the present invention.

The present invention is employed in a system such as that described in the previously-cited U.S. Pat. No. 5,592,085 which provides a means for measuring the strain in gyromagnetic materials, such as tissues, using MR methods and apparatus. The present invention may also be employed with other medical imaging modalities including, but not limited to, ultrasound. Referring to FIG. 1, a subject to be examined 10 is placed in the bore 12 of an MRI system magnet 14 and is subjected to magnetic fields produced by a polarizing coil 16, gradient coils 18 and an RF coil 20 during the acquisition of MR data from a region of interest in the subject 10. The homogeneity of these magnetic fields is important and any objects placed in the bore 12 must be carefully constructed of materials that will not perturb them.

The present system includes a passive actuator or driver 22 that is positioned over the region of interest in the subject 10 and secured thereto by strap 23. Passive actuator 22 is connected through a tube 24 to be in fluid communication with a remotely located active acoustic driver assembly 26. The acoustic driver assembly 26 is remote from the bore 12 of the magnet 14 in the sense that it is away from the strong magnet fields produced by the magnet 14 where its operation is not impeded by those fields, and where its operation will not perturb the MRI system magnetic fields. The acoustic driver assembly 26 is electrically driven by a waveform generator and amplifier 28, which in turn is controlled by the pulse sequencer in the MRI system control 30. The MRI system control 30 directs the MRI system to perform an MRE scan by driving the RF coil 20, and the gradient coils 18 in the magnet assembly 14 to perform a series of pulse sequences, while enabling the waveform generator 28 at the proper moment during each pulse sequence to apply an oscillatory stress to the subject 10 as described in the above-cited U.S. Pat. No. 5,592,085. The acoustic driver assembly 26 and the waveform generator and amplifier 28 may be housed in the same enclosure 31.

In particular, using the above-described system, the physical properties of tissue can be measured using MR elastography by applying a stress (e.g., tension, pressure, or shear) and observing the resulting strain (e.g., elongation, compression, rotation). By measuring the resulting strain, elastic properties of the tissue such as Young's modulus, Poisson's ratio, the shear modulus, and the bulk modulus can be calculated. By applying the stress in all three dimensions and measuring the resulting strain, the elastic properties of the tissue can be defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Figure 2A:
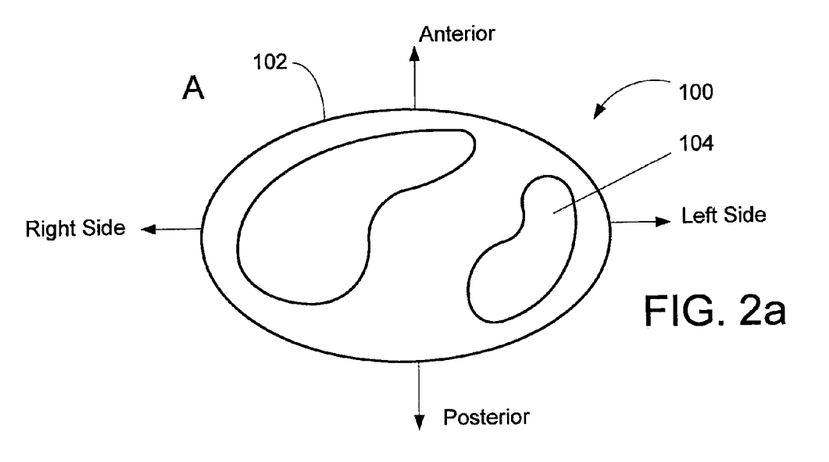
FIGS. 2a-2c illustrate transverse (or axial) cross-sectional views of a torso of a subject taken across the abdomen having a driver system in accordance with the present invention attached thereto.
Figure 2B:
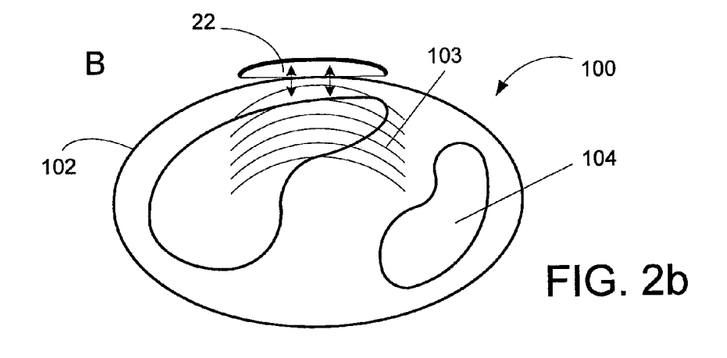
Figure 2C:
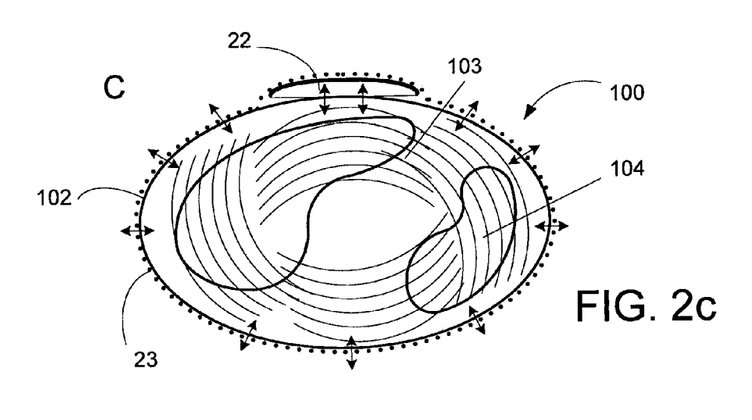

Referring now to FIGS. 2a-2c, cross-sectional views of the torso 100 of subject 10 taken across the abdomen are provided to illustrate an example application of the present system.

Each view is taken from an inferior position of subject 10. A posterior portion of subject 10 is positioned at the bottom of each figure. Each cross-section shows liver 102, with a largest portion of liver 102 being positioned on a right-side of subject 10.

To generate shear waves 103 within the liver 102, or other abdominal organs, passive actuator 22 is first positioned directly over liver 102 over the thorax of subject 10. As illustrated in FIG. 2b, passive actuator 22 may be positioned over the largest portion of the liver 102 on the right side of subject 10. Passive actuator 22 contacts the body wall of subject 10 and the vibrations generated by passive actuator 22 are communicated to liver 102 through the body wall. As shown in FIG. 2b, however, shear waves 103 generated by passive actuator 22, when applied to the body wall of subject 10, are constrained within a relatively small area. As illustrated, shear waves 103 are only formed adjacent to the actuator 22 and only penetrate a portion of liver 102 in the body cavity of subject 10.

In FIG. 2c, strap 23 (shown as a dashed line) is positioned around a circumference of subject 10 and around passive actuator 22. Strap 23 includes an inelastic or substantially inelastic material and is disposed around subject 10 to firmly hold passive actuator 22 against the body wall of subject 10 during operation of the present system. In one implementation, strap 23 includes a belt-like band having a width of approximately 4-6 inches that is disposed around subject 10 and passive actuator 22. Alternatively, strap 23 may be connected to passive actuator 22, or passed through a portion of passive actuator 22 to form a connection thereto and to secure passive actuator 22 against subject 10.

With strap 23 installed around subject 10 and passive actuator 22, once energized, passive actuator 22 causes cyclic variations in the tension of strap 23 around the circumference of subject 10. The variations in tension in strap 23 are modulated by those of acoustic driver assembly 26 and passive actuator 22 and improve the efficiency of energy transfer between passive actuator 22 and subject 10. Specifically, the variations in tension of strap 23 create further vibrations throughout the body of subject 10. In other words, strap 23 becomes a passive driver in and of itself. In the upper abdomen, the vibrations of strap 23 cause the body wall and lower rib cage of subject 10 to vibrate and become acoustic wave sources themselves. Additional cyclic pressure variations are also generated across the diaphragm, which leads to further enhanced generation of shear waves 103 within the liver 102, spleen 104, and other abdominal organs.

In this configuration, the primary role of passive actuator 22 is to generate cyclic variations in the tension of strap 23, not to stimulate a portion of subject 10. Strap 23 then communicates those vibrations to subject 10 and the internal organs of subject 10. Because strap 23 is the primary source of vibration energy in the present system, many other driver designs, possibly including active driver systems, may be used in combination with strap 23 to generate equivalent results. In some implementations, passive actuator 22 may include a vertical or horizontal driver structure, or a combination of vertical and/or horizontal drivers may be used in combination with strap 23.

Referring back to FIG. 1, in another implementation, the system is used to perform medical imaging of subject 10 positioned supine within MRI system magnet 14. Subject 10 lies on an examination surface in a supine position (as illustrated in FIG. 1), with a posterior portion of the torso of subject 10 being in contact with the scanner tabletop. In that configuration, strap 23 is primarily effective in transferring energy within the anterior and lateral free regions of the torso. As such, strap 23 may be formed around only the anterior and lateral portions of the circumference of subject 10 and attached to fixed anchor or mount points on the examination surface or other portion of the MRI system. Alternatively, strap 23 may be mounted to the source of vibration, such as a fixed passive driver. Generally, in this configuration, strap 23 is mounted at the lateral sides of the scanner table.

Therefore, the present system uses a strap 23 formed around a passive driver 22 or otherwise connected to a passive driver 22 to improve the transfer of energy between the passive driver 22 and the subject 10. The strap 23 enhances the coupling between the passive driver 22 and a side wall of the body of the subject 10, which results in more uniform illumination of the internal organs (including the liver 102) with shear waves 103, and also generates shear waves within other internal organs, such as the spleen 104. In some cases, the internal structure of the subject, such as the ribs or diaphragm, facilitate the formation and distribution of shear wave energy throughout the liver 102 and other internal organs.

Figure 3:
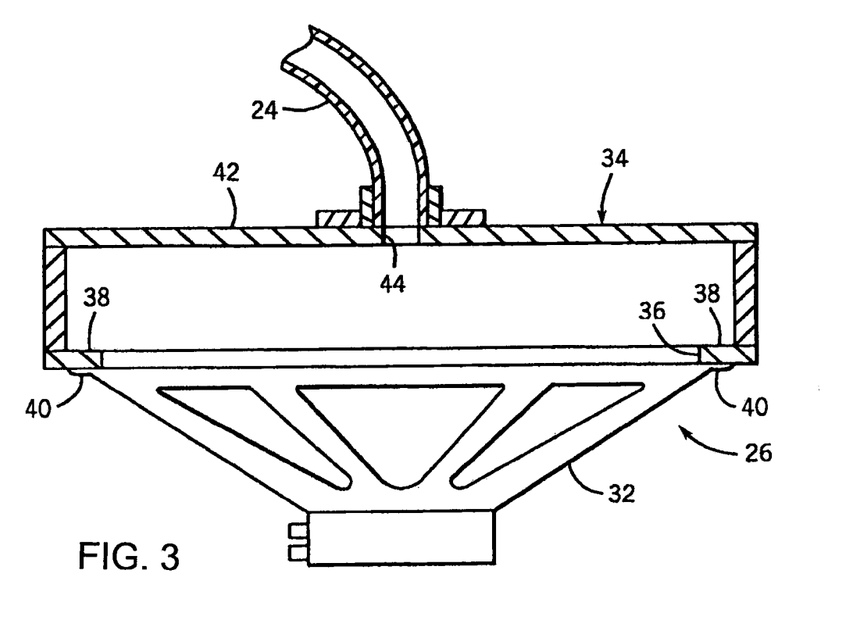
FIG. 3 is a cross-sectional view of an active driver used in the system of FIG. 1.

Referring to FIG. 3, an exemplary acoustic driver assembly 26 of the present system is comprised of a loudspeaker 32 mounted on one side of a thin enclosure 34. Acoustic driver assembly 26 generates acoustic energy which is communicated to passive actuator 22 where it is converted into mechanical energy. The enclosure 34 is constructed of a rigid material such as polycarbonate, and in one implementation it is a rectangular enclosure having a dimension of 18"×18"×1.5". A large opening 36 is formed in one wall 38 of the enclosure 34 and the flange 40 on the loudspeaker 32 fastens to this wall such that the speaker 32 directs acoustic energy directly into the enclosure 34.

One end of the tube 24 connects to the opposite wall 42 of enclosure 34 and is acoustically coupled to its interior by an output opening 44. As a result, the acoustic energy produced by the loudspeaker 32 is directly coupled to one end of the tube 24 through the thin enclosure 34.

The tube 24 is made of a material which is flexible, but which is not elastic. The flexibility enables it to be fed along a winding path between the subject 10 in the magnet 14 and the remote site of the acoustic driver assembly 26. In one implementation, the tube 24 is 20 feet long and has an inside diameter of 1.0 inches. It is made of a clear vinyl material sold under the trademark "TYGON" and has a wall thickness of approximately one-eighth inch. TYGON is a registered trademark of Norton Company of Worchester, Mass. It is nonelastic such that it does not stretch in response to the variations in air pressure caused by the acoustic energy it conveys. As a result, the acoustic energy is efficiently conveyed from the driver assembly 26 to the passive actuator 22.

Figure 4:
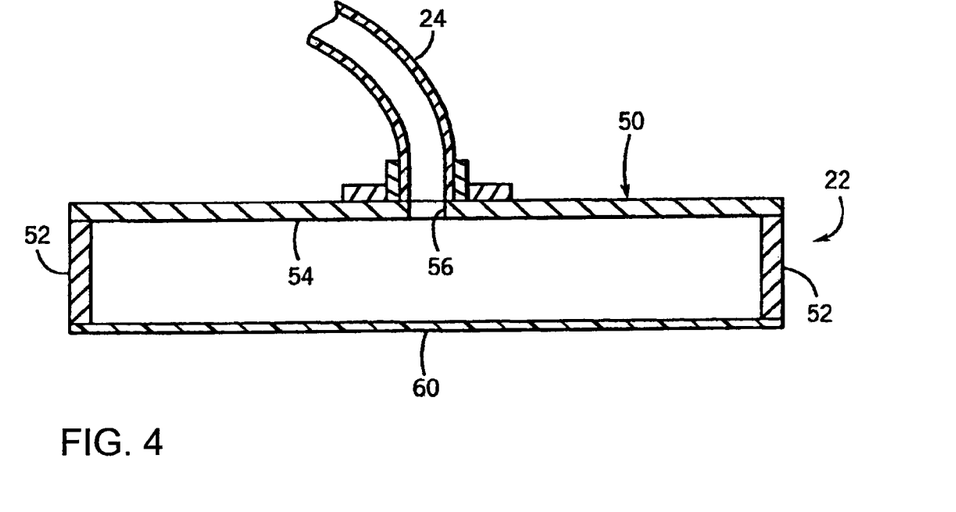
FIG. 4 is a cross-sectional view of a passive actuator used in the system of FIG. 1.

Referring to FIG. 4, an example passive actuator 22 of the present system includes a cylindrical shaped enclosure 50 connected to the end of the tube 24. The size of this enclosure 50 will vary depending on the particular clinical application, for example, ranging from 1 to 10 inches in diameter. The enclosure 50 is formed by a rigid, cylindrical outer wall 52 and a rigid circular end wall 54 that connects to one end of the outer wall 52. An input hole 56 is formed in the outer wall 52 or end wall 54 to acoustically couple the tube 24 to the interior chamber of the enclosure 50. Walls 52 and 54 are made of a polycarbonate or other nonferrous, nonelectrically conducting material which is both rigid and relatively "invisible" to the magnetic fields produced in the bore 12 of the magnet 14.

Stretched across the other end of the cylindrical outer wall 52 is a flexible membrane 60. The membrane 60 can be made of a rubber or any sufficiently elastic material, but in one implementation it is a very thin sheet (10-20 micron thick) of a polycarbonate material. This flexible membrane 60 rests against the surface of the subject 10 and vibrates in response to the acoustic energy received through the tube 24. The variations apply an oscillating stress to the subject's skin which is conveyed into the region of interest. The space, including the interior of tube 24 and the interior of enclosures 34 and 50, is rigidly defined and completely enclosed. As a result, vibrations of the loudspeaker cone in the driver assembly 26 are efficiently conveyed acoustically to the flexible membrane 60 in the passive actuator 22.

Because the passive actuator 22 is constructed only of materials that will not perturb magnetic fields, and because it does not require the use of electric current to operate, it can be freely located anywhere within the bore 12 of the magnet 14. There is no need to align it in any particular direction to operate, and it can be placed very close to the region of interest without producing image artifacts.

Generally, the present system may be implemented using any passive driver configuration that may be fixed to a body wall of subject 10 using strap 23, although passive drivers having a "drum-like" configuration may be desirable in some applications. Other passive drivers include those illustrated in FIGS. 5-7, in which passive actuator 22 includes a disk-shaped back plate 200 and a circular rim 202. The back plate 200 is made of a flexible polymer such as polycarbonate or ABS plastic, and as shown best in FIG. 7, it can bend to fit the curved contour of a subject 10 when strapped into place over the region of interest.

Figure 5:
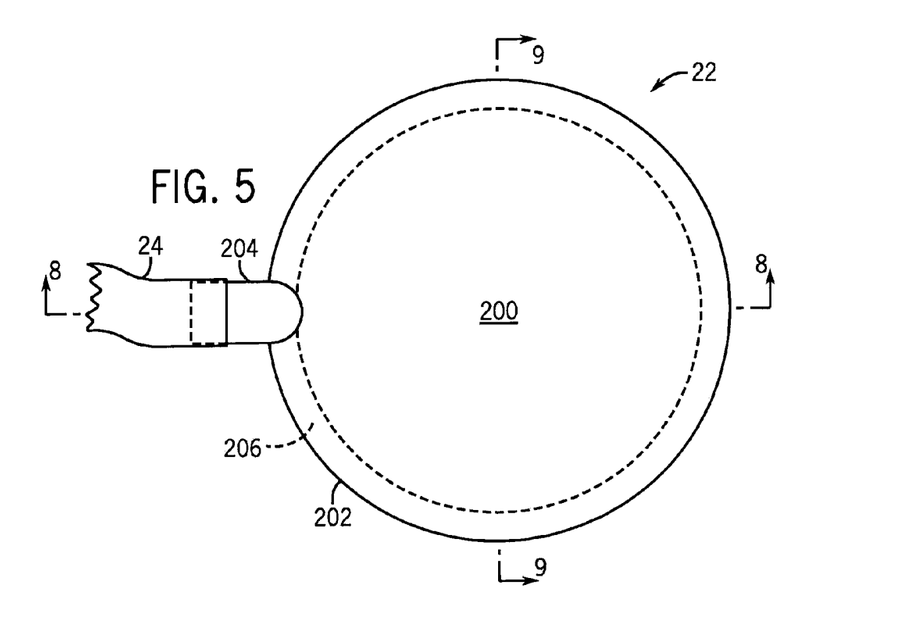
FIG. 5 is a top plan view of an alternative form of the passive actuator which forms part of the system of FIG. 1.
Figure 6:
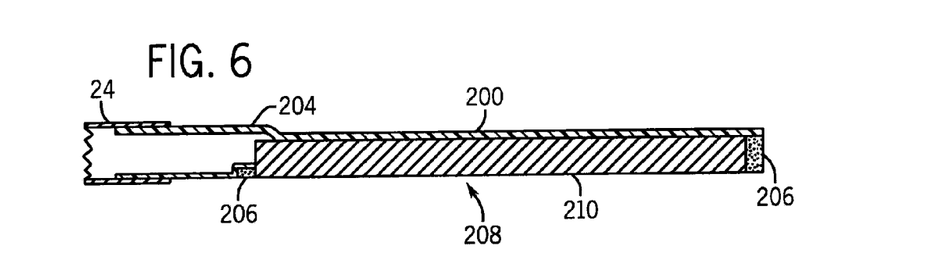
FIG. 6 is a cross-sectional view of the passive actuator of FIG. 5 taken along line 6-6.
Figure 7:
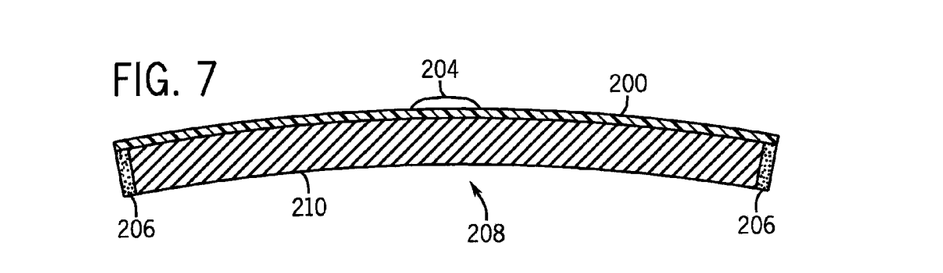
FIG. 7 is a cross-sectional view of the passive actuator of FIG. 5 taken along line 7-7 showing the actuator slightly flexed.

An integrally molded intake pipe 204 is formed on the rim 202 of the back plate 200 and its diameter is such that the flexible tube 24 from the active driver 26 makes a tight, frictional attachment to its outer surface. The intake pipe 204 delivers the acoustic energy conveyed by the tube 24 to the space beneath the back plate 200.

An annular-shaped sealing ring 206 fastens to the bottom surface of the back plate 200 and extends downward therefrom to form the wall of an acoustic cavity indicated generally at 208 that acoustically communicates with the intake pipe 204. The sealing ring 206 is made of a closed cell foam such as that sold under the trademark "Polycell" that is injection molded in a one-step process. Polycell is a registered trademark of Imperial Chemical Industries of London, UK. The sealing ring 206 is very flexible and conforms to the contour of the subject 10 without creating uncomfortable pressure points. The bottom edge of the sealing ring 206 engages the subject 10 and also provides a flexible, comfortable seal around the rim 202 of the back plate 200 that confines the acoustic energy delivered by the tube 24 to the acoustic cavity 208.

To keep the back plate 200 spaced from the subject 10 and to thereby maintain the integrity of the acoustic cavity 208 when the device is placed against and/or wrapped around a complex contoured surface, the acoustic cavity 208 is filled with an open cell foam insert 210. The insert 210 may be a solid piece of acoustically transparent material as shown, or it may be cut in a pattern. The insert 210 maintains a spacing between the subject and the back plate 200 while enabling the acoustic energy delivered through the tube 204 to be conveyed with the least possible attenuation to the subject 10 which the insert 210 engages.

With this passive actuator 22 implementation, there is no flexible membrane fastened to the passive actuator 22. Instead, a seal is made with the subject's skin around the rim 202 and the enclosed skin acts as a flexible membrane that couples the acoustic pressure waves in the cavity 208 to the tissues underneath.

Figure 8:
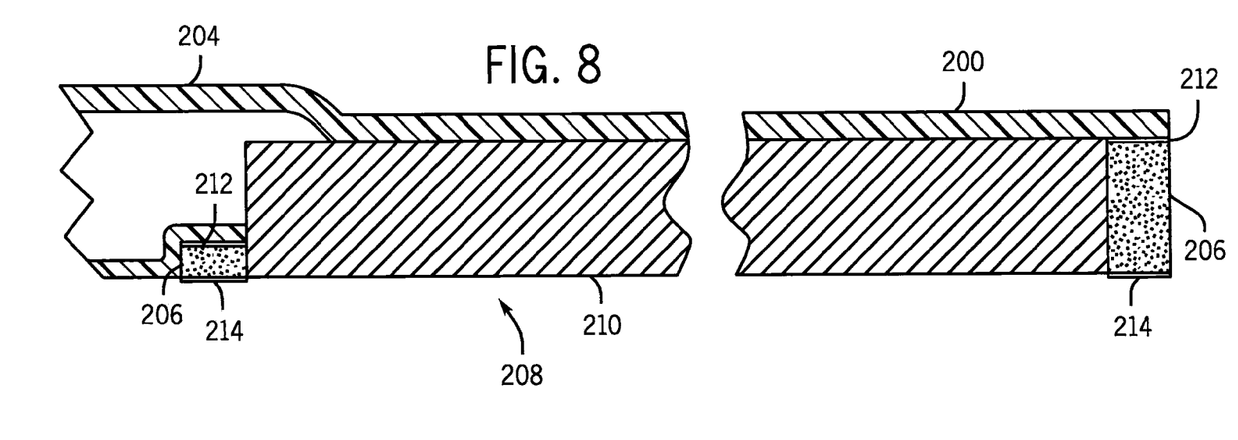
FIG. 8 is a cross-sectional view showing a variation of the passive actuator of FIG. 5.

A number of variations are possible for the passive actuator 22 implementation. Referring to FIG. 8, for example, the sealing ring 206 may be attached to the rim of the back plate 200 using a layer of pressure-sensitive adhesive 212. This enables the sealing ring 206 and attached foam insert 210 to be "peeled" from the back plate 200 after use and either cleaned or discarded. A new foam assembly can then be aligned with the back plate 200 and pressed into place for use with the next patient.

A less aggressive pressure sensitive adhesive 214 may also be formed on the opposite side of the sealing ring 206 that engages the subject 10 being imaged. When the passive actuator 22 is positioned on the subject 10 to be imaged, pressure is applied around the rim of the back plate 200 to engage the pressure-sensitive adhesive 214 and provide a good acoustic seal with the subject 10.

Figure 9:
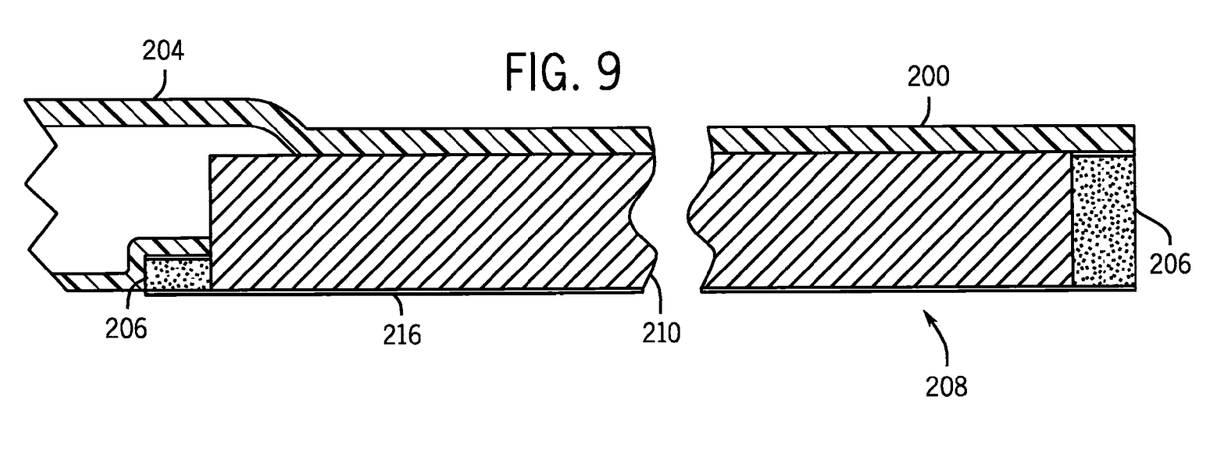
FIG. 9 is a cross-sectional view showing another variation of the passive actuator of FIG. 5.

Referring to FIG. 9, another variation is to attach a flexible membrane 216 to the bottom surface of the sealing ring 206. The membrane 216 stretches across the entire acoustic cavity 208 to seal it from the surroundings. The membrane 216 conveys the acoustic pressure waves in the acoustic cavity 208 substantially uniformly to the subject 10. The membrane 216 may be attached to the sealing ring with a pressure-sensitive adhesive that enables it to easily be replaced after use, or the sealing ring 206, insert 210 and membrane 216 may be formed as an integral unit that can be peeled away from the back plate 200 as described above.

Figure 10:
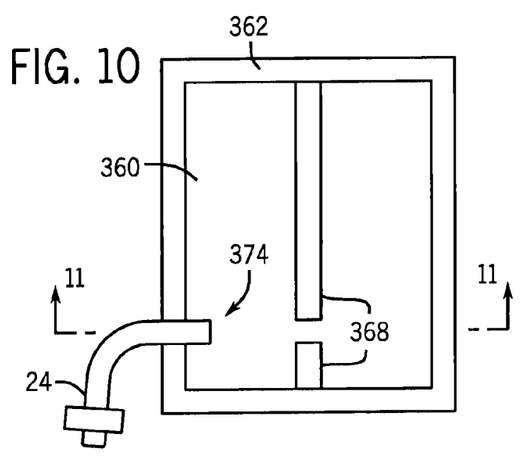
FIG. 10 is a bottom plan view of a third alternative of the passive actuator which forms part of the MRI system of FIG. 1.
Figure 11:
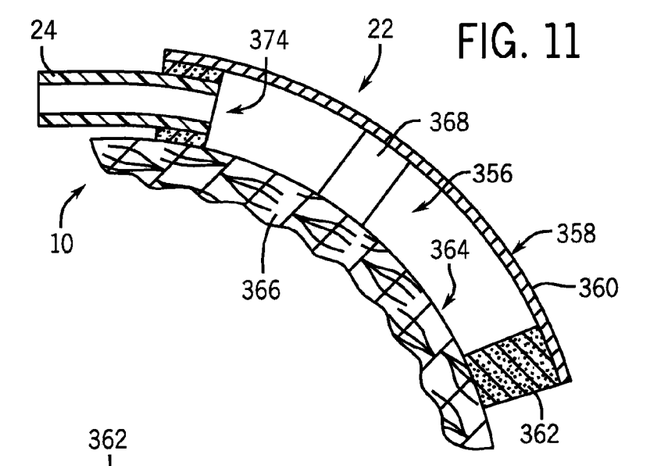
FIG. 11 is a cross-sectional view of the passive actuator of FIG. 10 taken along line 11-11 showing the actuator on a subject and slightly flexed.

Referring to FIGS. 10 and 11, another implementation of the passive actuator 22 includes a generally rectangular shaped enclosure 358 that is placed over a region of interest of a subject 10 to be examined. The size and shape of this enclosure 358 can vary depending on the particular clinical application and the particular region of interest to be examined. The enclosure 358 is flexible so that it can be shaped to better fit the anatomical shape of the subject 10.

As shown, the enclosure 358 of the passive actuator 22 is formed by a rectangular outer wall 362 and a back plate 360 joined together to define an interior chamber 356 when the enclosure 358 rests on the surface of a subject 10 to be examined. The back plate 360 is made with a nonferrous, nonelectrically conducting flexible material such as plastic, styrofoam, cardboard, and the like. The outer wall 362 is made of a relatively compliant material including, but not limited to, closed cell foam or rubber. Both the back plate 360, and the wall 362 are relatively "invisible" to the magnetic fields produced in the bore 12 of the magnet 14. The back plate 360 or the outer wall 362 includes a hole or port 374 configured to be connected to the tube 24.

The passive actuator 22 is placed against a surface 364 of the skin 366 of the subject 10 such that the enclosure 358 and the subject 10 define a fully enclosed chamber 356. To effectuate an airtight seal, the passive actuator 22 is pressed firmly against the skin 366 and may be held in place with a strap 23 disposed around a circumference of the subject 10. Because of the compliant nature of the materials used, the back plate 360 flexes and the outer wall 362 compresses as necessary to conform to the anatomical shape of the subject 10. A silicone gel, or similar material, may also be used to help create an airtight seal.

Standoffs 368, formed of rigid or slightly compressible material, are mounted to the back plate 362 of the enclosure 358 and extend downward a suitable depth into the chamber 356 to engage the surface 364 of the subject 10. The standoffs 368 ensure that the surface 364 of the subject 10 is spaced from the back plate 360 where there is substantial curvature. Although the standoffs 368 shown in FIG. 10 divide the chamber 356, the standoffs 368 may be formed in alternate shapes and arranged in a variety of placements as long as there is minimal interference with or dampening of the oscillating pressure waves.

Figure 12:
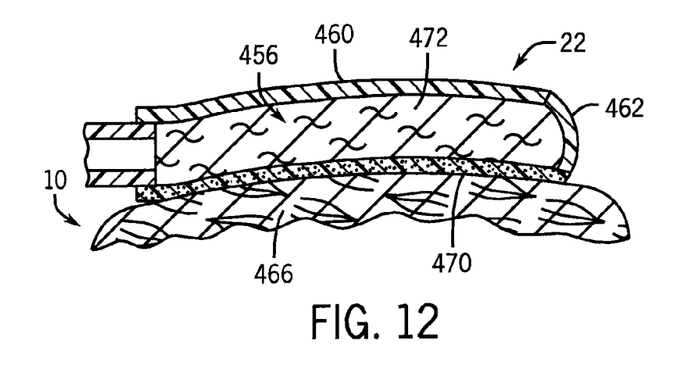
FIG. 12 is a cross-sectional view of a fourth alternative implementation of the passive actuator which forms part of the system of FIG. 1.

Referring to FIG. 12, another embodiment of a flexible passive acoustic actuator 22 includes a flexible membrane 470. The passive actuator 22 further includes a thin cylindrical chamber 456 defined by an end wall 460, side walls 462, and membrane 470. The end wall 460 is formed from a flexible material such as thin polycarbonate plastic, styrofoam, foam rubber, and so on. The side walls 462 are made of a flexible and relatively compliant material such as closed cell or open cell foam or rubber. The membrane 470 is made of rubber or another sufficiently elastic material. The chamber 456 is filled with a highly porous yet flexible material 472, such as a loose, woven fabric or a material such as used in a furnace filter.

The flexible membrane 470 is placed against the skin 466 of the subject 10 and, along with the entire passive actuator 22, conforms to the shape of the subject 10. The diaphragm 470 vibrates in response to the acoustic energy received through the tube 24. The vibrations apply an oscillating stress to the skin 466 of the subject 10 which is conveyed into the region of interest as shear waves. The material 472 in the chamber 456 maintains an appropriate spacing between the skin 466 and the end wall 460 and does not impede the pressure waves traveling therethrough.

Thus, the present system provides a mechanism for introducing vibrations into abdominal organs for performing MR elastography or other medical imaging. Specifically, a passive actuator or driver is provided that is configured to be placed against the thorax of the subject above, for example, the ribcage and induces a vibration against the subject's body. The vibration can be enhanced with the addition of a strap disposed around the subject and the actuator. The vibration is communicated to the subject's ribcage, which operates as an extension of the passive driver creating cyclic pressure variations across the diaphragm, between, for example, the thorax and abdomen. Shear waves are generated in the abdomen via mode conversion at multiple locations, particularly where the diaphragm contacts upper abdominal organs and at retroperitoneal locations. The system may operate to eliminate unexpected preload of the abdominal organs, further enhancing the reliability of shear stiffness measurements with MRE.

In addition, the system may provide for increased variations in the strength of the transdiaphragmatic pressure by placing a second passive driver, driven 180 degrees out of phase, against the abdominal wall. In this case, a strap mechanism may be placed around the subject to secure the driver to the subject. Using the strap, one or more drivers may be secured to the subject's body at various positions to optimize the location of the drivers depending upon the application. For example, when imaging the kidneys, the strap may be used to position one or more passive drivers to provide optimal energy transfer from the drivers to the kidneys to improve image quality. The system may be used in combination with MR or ultrasound medical imaging.

While one or more embodiments of the present invention have been illustrated in detail, the skilled artisan will appreciate that modifications and adaptations to those embodiments may be made without departing from the scope of the present invention as set forth in the following claims.

The invention claimed is:

1. A system for producing a stress on a subject while performing a magnetic resonance elastography scan in a magnetic resonance imaging (MRI) system, the combination comprising:
an active driver operable to produce acoustic energy configured for a magnetic resonance elastography (MRE) process;
a passive actuator configured to be positioned in the MRI system and be coupled to the subject;
a tube coupling the active driver to the passive actuator to deliver the energy produced by the active driver to the passive actuator; and
a strap coupled to the passive actuator and configured to be disposed around the subject, the strap including a substantially inelastic material configured to convert the energy delivered to the passive actuator from the tube into shear waves with the subject for use in the MRE process.

2. The system of claim 1, wherein the passive actuator includes:
a back plate formed of a flexible material; and
a wall attached to the rim of the back plate to define a perimeter of a cavity, the wall including a flexible foam material that engages the subject and conforms to the surface thereof.

3. The system of claim 2, wherein the flexible foam material of the wall forms a seal with the subject such that the acoustic energy delivered to the cavity vibrates the skin of the subject.

4. The system of claim 2, wherein the flexible foam material of the wall is removable from the back plate.

5. The system of claim 2, including a flexible membrane attached to the flexible foam material of the wall around the cavity.

6. The system of claim 2, wherein the cavity includes an insert to space the back plate from the surface of the subject.

7. The system of claim 6, wherein the flexible foam material of the wall is a closed cell foam and the insert is an open cell foam.

8. The system of claim 1, wherein the strap has a width between 4 to 6 inches.

9. The system of claim 1, wherein the MRI system includes an examination surface and the strap is coupled to the examination surface.

10. A system for producing a stress on a subject undergoing an imaging procedure, comprising:
an actuator configured to be disposed over a thorax of the subject and being configured to receive energy to be applied to the subject of an examination; and
a strap configured to be disposed around the subject, the strap including a substantially inelastic material and being coupled to the actuator to convert the energy received by the actuator into cyclic variations of a tension of the strap to generate shear waves within the subject configured for the imaging procedure.

11. The system of claim 10, wherein the actuator includes:
a back plate formed of a flexible material; and
a wall attached to the rim of the back plate to define a perimeter of a cavity, the wall including a flexible foam material that engages the subject and conforms to the surface thereof.

12. The system of claim 11, including a flexible membrane attached to the flexible foam material of the wall around the cavity.

13. The system of claim 11, wherein the cavity includes an insert to space the back plate from the surface of the subject.

14. The system of claim 13, wherein the flexible foam material of the wall is a closed cell foam and the insert is an open cell foam.

15. The system of claim 10, wherein the strap has a width between 4 to 6 inches.

16. The system of claim 10, wherein the strap is coupled to an examination surface of an MRI system.

17. A method of generating shear waves within an abdomen of a subject for medical imaging using an actuator for magnetic resonance elastography (MRE) in a magnetic resonance imaging (MRI) system, comprising:
positioning the actuator against a body wall of a thorax of the subject over a ribcage of the subject, the actuator being configured to receive acoustic energy;
securing a strap around a circumference of the subject and over the actuator to hold the actuator against the body wall of the subject, the strap including a substantially inelastic material;
transmitting acoustic energy to the actuator to generate mechanical vibrations of the actuator; and
using the mechanical vibrations of the actuator to generate cyclic variations of a tension of the strap, the cyclic variations of the tension of the strap being communicated to the ribcage of the subject, the ribcage generating pressure variations within the abdomen of the subject which are communicated to internal organs of the abdomen of the subject for MRE of an internal organ of the abdomen of the subject.

18. The method of claim 17, including coupling the strap to an examination surface of the MRI system.

19. The method of claim 18, wherein the strap has a width between 4 to 6 inches.

* * * * *